United States Patent [19]

Machida et al.

[11] Patent Number: 4,468,394

[45] Date of Patent: Aug. 28, 1984

[54] CEPHALOSPORIN COMPOUNDS

[75] Inventors: Yoshimasa Machida, Ibaraki; Isao Saito, Tokyo; Isao Sugiyama, Tokyo; Shigeto Negi, Tokyo; Seiichiro Nomoto, Tokyo; Hironori Ikuta, Tokyo; Hiroshi Yamauchi, Ibaraki; Kyosuke Kitoh, Saitama, all of Japan

[73] Assignee: Eisai Co., Ltd., Tokyo, Japan

[21] Appl. No.: 363,778

[22] Filed: Mar. 31, 1982

[30] Foreign Application Priority Data

Apr. 2, 1981 [JP] Japan .................................. 56-48437
Apr. 2, 1981 [JP] Japan .................................. 56-48438

[51] Int. Cl.³ .................. A61K 31/545; C07D 501/04; C07D 501/46; C07D 501/56
[52] U.S. Cl. .................................. 424/246; 260/239.1; 424/256; 424/258; 424/271; 544/21; 544/25; 544/27; 544/28; 544/30
[58] Field of Search .................. 260/239.1; 544/21, 25, 544/27, 28, 30; 424/246, 256, 271, 258

[56] References Cited

U.S. PATENT DOCUMENTS

| | | | |
|---|---|---|---|
| 3,939,150 | 2/1976 | Murakami et al. | 260/239.1 |
| 3,951,955 | 4/1976 | Tobiki et al. | 260/239.1 |
| 4,005,075 | 1/1977 | Yamada et al. | 260/239.1 |
| 4,159,268 | 6/1979 | Curran et al. | 260/239.1 |
| 4,303,664 | 12/1981 | Ono et al. | 424/271 |
| 4,317,774 | 3/1982 | Sassiver et al. | 260/239.1 |
| 4,320,133 | 3/1982 | Hamberger et al. | 424/269 |
| 4,341,703 | 7/1982 | Sassiver et al. | |

*Primary Examiner*—Natalie Trousof
*Assistant Examiner*—Vera C. Clarke
*Attorney, Agent, or Firm*—Wenderoth, Lind & Ponack

[57] ABSTRACT

A compound represented by the formula:

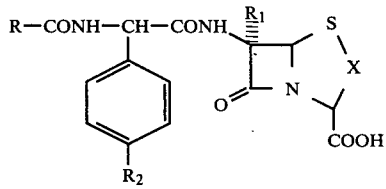

wherein $R_1$ is hydrogen or methoxy; $R_2$ is hydrogen or hydroxy; R is

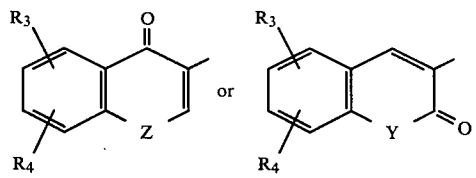

wherein $R_3$ and $R_4$ are hydroxy or acyloxy, Y is oxygen, sulfur or $>N-R_5$ wherein $R_5$ is hydrogen or lower alkyl, and Z is sulfur or $>N-R_5$ wherein $R_5$ has the same meanings as defined above; and X is

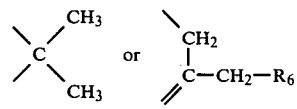

wherein $R_6$ is acyloxy or nitrogen-containing heterocyclicthio which may have substituent(s), a pharmaceutically acceptable salt thereof, and a carboxylic ester thereof.

This compound has improved antibacterial activity against *Kleb. pneumoniae* and *Pseud. aeruginosa*.

14 Claims, No Drawings

CEPHALOSPORIN COMPOUNDS

The present invention relates to novel compound represented by the formula:

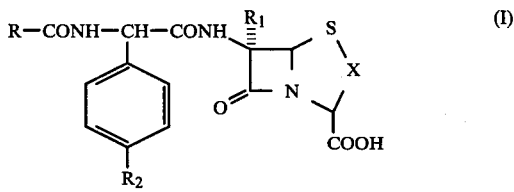

wherein $R_1$ is hydrogen or methoxy; $R_2$ is hydrogen or hydroxy; R is

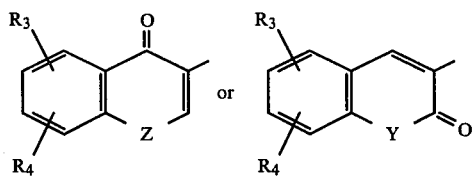

wherein $R_3$ and $R_4$ are hydroxyl or acyloxy, Y is oxygen, sulfur or $>N-R_5$ wherein $R_5$ is hydrogen or lower alkyl, and Z is sulfur or $>N-R_5$ wherein $R_5$ has the same meanings as defined above; and X is

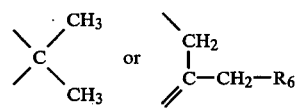

wherein $R_6$ is acyloxy or nitrogen-containing heterocyclic-thio which may have substituent(s), a pharmaceutically acceptable salt thereof, and a carboxylic ester thereof.

More particularly, the present invention relates to novel compounds represented by the formula:

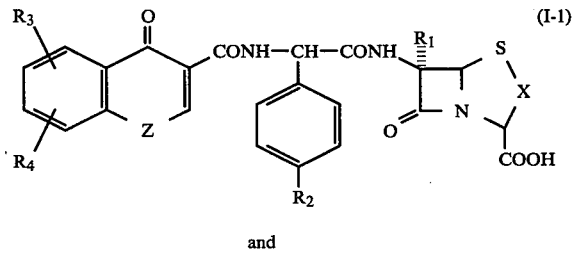

and

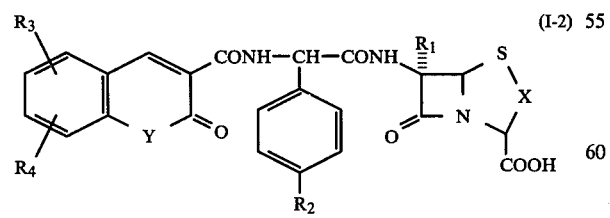

wherein $R_1$, $R_2$, $R_3$, $R_4$, X, Y and Z have the same meanings as defined above, pharmaceutically acceptable salts thereof, and carboxylic esters thereof.

In the above-mentioned formulae, the acyloxy group represented by $R_3$, $R_4$ and $R_6$ includes, for example, acetoxy and propionyloxy; and the lower alkyl group represented by $R_5$ includes, for example, methyl, ethyl, n-propyl, and i-propyl. With reference to the wording "nitrogen-containing heterocyclic-thio which may have substituent" which is represented by $R_6$, it means a substituted or unsubstituted heterocyclic-thio group containing one or more nitrogen atoms as hetero atoms. The said nitrogen-containing heterocyclic group may be a mono- or polycyclic group. These nitrogen-containing heterocyclic groups may contain one or more nitrogen atoms only as hetero atom or atoms, or they may also contain another hetero atom or atoms such as sulfur and oxygen in addition to nitrogen. Examples of such heterocyclic groups include pyrrolyl, pyridyl and N-oxide thereof, imidazolyl, pyrazolyl, pyrimidinyl, pyridazinyl, 1H-1,2,4-triazolyl, 4H-1,2,4-triazolyl, 1H-1,2,3-triazolyl, 2H-1,2,3-triazolyl, 1H-tetrazolyl, 2H-tetrazolyl, thiazolyl, 1,2,3-thiadiazolyl, 1,2,4-thiadiazolyl, 1,3,4-thiadiazolyl, oxazolyl, 1,3,4-oxadiazolyl, 1,2,5-oxadiazolyl, morpholino, benzothiazolyl, and benzoxazolyl. These groups may have one or more substituents. The examples of such substituents are alkyl group such as methyl, ethyl, propyl, and isopropyl; amino group; dialkylaminoalkyl group such as dimethylaminoethyl, dimethylaminomethyl, and diethylaminoethyl; carboxyalkyl group such as carboxymethyl and carboxyethyl; and sulfoalkyl groups such as sulfomethyl and sulfoethyl.

The pharmaceutically acceptable salts of the compound of the formula (I) include sodium salt, potassium salt, calcium salt, ammonium salt, triethylamine salt, dicyclohexylamine salt, and procain salt.

The carboxylic esters of the compound of the formula (I) include pivaloyloxymethyl ester, phthalidyl ester, methoxymethyl ester, and the like.

There are disclosed penicillin compounds having a γ-quinolone skeleton in which Z in the above formula is $>N-R_5$ in Japanese Patent Laid-Open Nos. 50-17994 (1975), 50-17995 (1975), 50-23036 (1975), and 50-23037 (1975), and penicillin and cephalosporin derivatives having coumarin skeleton in which Y in the above formula is oxygen in Japanese Patent Laid-open Nos. 53-40793 (1978), 53-87389 (1978), and 54-122288 (1979).

As compared with these compounds, the compound of this invention has a greatly improved antibacterial activity to *Kleb. pneumoniae* and *Pseud. aeruginosa* because it has such a structure that the γ-quinolone skeleton, thiochromone skeleton coumarin skeleton, thiocoumarin skeleton, or α-quinolone skeleton is substituted with two specific groups represented by $R_3$ and $R_4$, or hydroxyl groups and acyloxy groups.

The compound of this invention can be produced by reacting a compound of the formula:

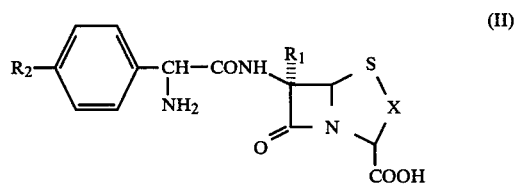

wherein $R_1$, $R_2$ and X have the same meanings as defined above, or a salt or hydrate thereof, with a compound represented by the formula:

R—COOH (III)

wherein R is

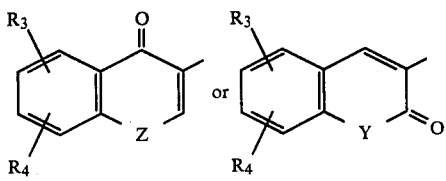

wherein $R_3$ and $R_4$ are hydroxy or acyloxy, Y is oxygen, sulfur or $>N-R_5$ wherein $R_5$ is hydrogen or lower alkyl, and Z is sulfur or $>N-R_5$ wherein $R_5$ has the same meanings as defined above, or a reactive derivative thereof. The resulting compound may be converted into a salt or carboxylic ester.

In the case where the compound of formula (III) is a carboxylic acid, the above-mentioned reaction should preferably be carried out in the presence of a condensing agent such as N,N'-dicyclohexylcarbodiimide, N,N'-diethylcarbodiimide, N-cyclohexyl-N'-morpholinoethylcarbodiimide, ethyl phosphite ester, phosphorus oxychloride, and oxalyl chloride.

In the case where the compound of formula (III) is a reactive derivative of carboxylic acid, such reactive derivatives include acid halide such as acid chloride and acid bromide; symmetric acid anhydride; chlorocarbonic ester; mixed acid anhydride of trimethyl acetic acid and diphenyl acetic acid; active ester such as 2-mercaptopyridine, cyanomethanol, p-nitrophenol, 2,4-dinitrophenol, and pentachlorophenol; and active acid amide such as N-acylsaccharin and N-acylphthalimide.

The above-mentioned reaction may be carried out in an inert solvent in the presence or absence of a basic reagent or silylating reagent, at a temperature from $-50°$ C. to $50°$ C., preferably from $-20°$ C. to $30°$ C.

The inert solvent includes acetone, tetrahydrofuran, dimethylacetamide, dimethylformamide, dioxane, dichloromethane, chloroform, benzene, toluene, ethyl acetate, or mixtures thereof.

The basic reagent includes, for example, alkali hydroxides such as sodium hydroxide and potassium hydroxide; alkali hydrogen carbonates such as sodium hydrogen carbonate and potassium hydrogen carbonate; and amines such as triethylamine, pyridine, dimethylaniline, and N-methylmorpholine.

The silylating agent includes, for example, N,O-bis(-trimethylsilyl)acetamide, hexamethyldisilazane, and trimethylsilylacetamide.

The salt and carbonate ester can be produced in the usual way.

Among the compounds of this invention, the compound represented by the formula:

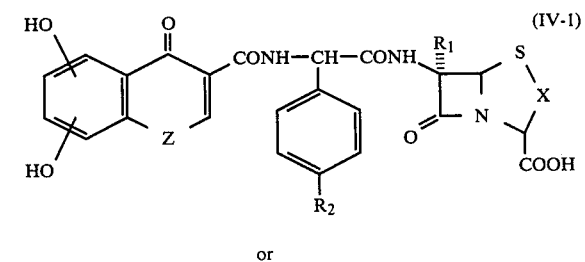

or

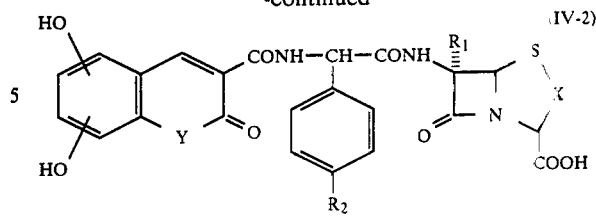

(wherein $R_1$, $R_2$ X, Y and Z have the same meanings as defined above) can be obtained by hydrolyzing the compound represented by the formula:

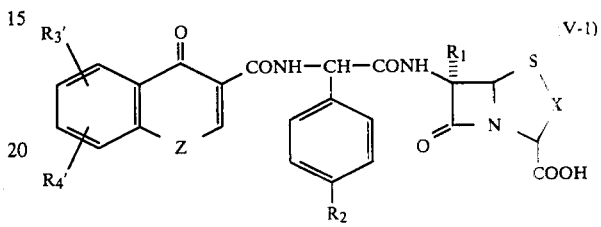

or

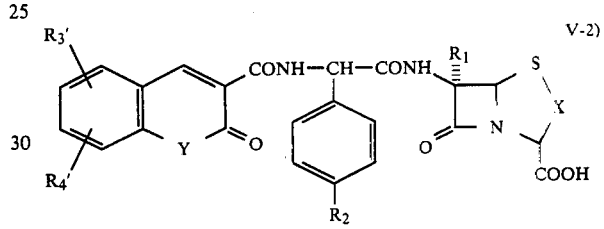

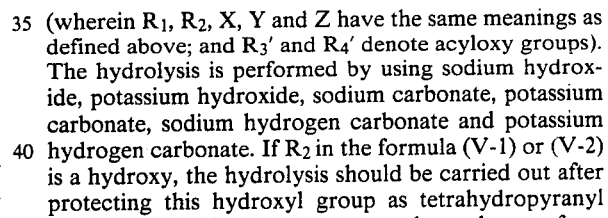

(wherein $R_1$, $R_2$, X, Y and Z have the same meanings as defined above; and $R_3'$ and $R_4'$ denote acyloxy groups). The hydrolysis is performed by using sodium hydroxide, potassium hydroxide, sodium carbonate, potassium carbonate, sodium hydrogen carbonate and potassium hydrogen carbonate. If $R_2$ in the formula (V-1) or (V-2) is a hydroxy, the hydrolysis should be carried out after protecting this hydroxyl group as tetrahydropyranyl ether or the like in order to prevent the acyl group from being migrated to this position during hydrolysis.

The compounds (I-1) and sodium salts thereof embodying the present invention are exemplified as follows:

7β-[D-2-(6,7-Diacetoxy-1,4-dihydro-4-oxoquinoline-3-carboxamide)-2-(4-hydroxyphenyl)acetamide]-3-(1-carboxymethyl-5-tetrazolyl)thiomethyl-3-cephem-4-carboxylic acid.

6β-[D-2-(6,7-Diacetoxy-1-ethyl-1,4-dihydro-4-oxoquinoline-3-carboxamide)-2-phenylacetamide]-penicillanic acid.

7β-[D-2-(6,7-Diacetoxy-1-ethyl-1,4-dihydro-4-oxoquinoline-3-carboxamide)-2-(4-hydroxyphenyl)acetamide]-3-acetoxymethyl-3-cephem-4-carboxylic acid.

7β-[D-2-(6,7-Diacetoxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

7β-[D-2-(6,7-Diacetoxy-1-ethyl-1,4-dihydro-4-oxoquinoline-3-carboxamide)-2-(4-hydroxyphenyl)acetamide]-3-(1-carboxymethyl-5-tetrazolyl)thiomethyl-3-cephem-4-carboxylic acid.

7β-[D-2-(6-Acetoxy-7-hydroxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid pivaloyl oxymethyl ester.

7β-[D-2-(6-Acetoxy-7-hydroxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

7β-[D-2-(6,7-Dihydroxy-1-ethyl-1,4-dihydro-4-oxoquinoline-3-carboxamide)-2-phenylacetamide]-3-(1-methyl-5-tetrazolyl)thiomethyl-3-cephem-4-carboxylic acid.

7β-[D-2-(6,7-Dihydroxy-1-ethyl-1,4-dihydro-4-oxoquinoline-3-carboxamide)-2-(4-hydroxyphenyl)acetamide]-3-(5-methyl-2-(1,3,4-thiadiazolyl)]thiomethyl-3-cephem-4-carboxylic acid.

7β-[D-2-(6,7-Dihydroxy-1-methyl-1,4-dihydro-4-oxoquinoline-3-carboxamide)-2-phenylacetamide]-7α-methoxy-3-[5-carboxymethyl-2-(1,3,4-thiadiazolyl)]thiomethyl-3-cephem-4-carboxylic acid.

7β-[D-2-(7,8-Dihydroxy-1-ethyl-1,4-dihydro-4-oxoquinoline-3-carboxamide)-2-(4-hydroxyphenyl)acetamide]-3-[5-carboxymethyl-2-(1,3,4-oxadiazolyl)]thiomethyl-3-cephem-4-carboxylic acid.

7β-[D-2-(6,7-Diacetoxy-4-oxo-4H-1-benzothiopyran-3-carboxamide)-2-(4-hydroxyphenyl)acetamide]-7α-methoxy-3-acetoxymethyl-3-cephem-4-carboxylic acid.

7β-[D-2-(6,7-Diacetoxy-4-oxo-4H-1-benzothiopyran-3-carboxamide)-2-(4-hydroxyphenyl)acetamide]-3-(1-methyl-5-tetrazolyl)thiomethyl-3-cephem-4-carboxylic acid.

7β-[D-2-(6,7-Diacetoxy-4-oxo-4H-benzothiopyran-3-carboxamide)-2-(4-hydroxyphenyl)acetamide]-3-(1-carboxymethyl-5-tetrazolyl)-thiomethyl-3-cephem-4-carboxylic acid.

7β-[D-2-(6,7-Dihydroxy-4-oxo-4H-1-benzothiopyran-3-carboxamide)-2-(4-hydroxyphenyl)acetamide]-3-(1-methyl-5-tetrazolyl)thiomethyl-3-cephem-4-carboxylic acid.

7β-[D-2-(6,7-Dihydroxy-4-oxo-4H-1-benzothiopyran-3-carboxamide)-2-(4-hydroxyphenyl)acetamide]-3-(1-carboxymethyl-5-tetrazolyl)-thiomethyl-3-cephem-4-carboxylic acid.

7β-[D-2-(6,7-Dihydroxy-4-oxo-4H-1-benzothiopyran-3-carboxamide)-2-(4-hydroxyphenyl)acetamide]-3-(1-sulfomethyl-5-tetrazolyl)-thiomethyl-3-cephem-4-carboxylic acid.

7β-[D-2-(6,7-Dihydroxy-4-oxo-4H-1-benzothiopyran-3-carboxamide)-2-phenylacetamide]-3-[5-carboxymethyl-2-(1,3,4-thiazolyl)]thiomethyl-3-cephem-4-carboxylic acid.

7β-[D-2-(6,7-Dihydroxy-4-oxo-4H-1-benzothiopyran-3-carboxamide)-2-(4-hydroxyphenyl)acetamide]-3-[5-carboxymethyl-2-(1,3,4-oxadiazolyl)]thiomethyl-3-cephem-4-carboxylic acid.

7β-[D-2-(6,7-Dihydroxy-4-oxo-4H-1-benzothiopyran-3-carboxamide)-2-(4-hydroxyphenyl)acetamide]-7α-methoxy-3-(1-carboxymethyl-5-tetrazolyl)thiomethyl-3-cephem-4-carboxylic acid.

6β-[D-2-(7,8-Dihydroxy-4-oxo-4H-1-benzothiopyran-3-carboxamide)-2-phenylacetamide]penicillanic acid.

7β-[D-(7,8-Dihydroxy-4-oxo-4H-1-benzothiopyran-3-carboxamide)-2-(4-hydroxyphenyl)acetamide]-3-(1-carboxymethyl-5-tetrazolyl)thiomethyl-3-cephem-4-carboxylic acid.

The compounds (I-2) and sodium salts thereof embodying the present invention are exemplified as follows:

6β-[D-2-(6,7-Diacetoxy-2-oxo-2H-1-benzopyran-3-carboxamide)-2-phenylacetamide]penicillanic acid.

7β-[D-2-(6,7-Diacetoxy-2-oxo-2H-1-benzopyran-3-carboxamide)-2-(4-hydroxyphenyl)acetamide]-3-acetoxymethyl-3-cephem-4-carboxylic acid.

7β-[D-2-(6,7-Diacetoxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid.

6β-[D-2-(6,7-Dihydroxy-2-oxo-2H-1-benzopyran-3-carboxamide)-2-phenylacetamide]penicillanic acid.

6β-[D-2-(6,7-Dihydroxy-2-oxo-2H-1-benzopyran-3-carboxamide)-2-(4-hydroxyphenyl)acetamide]penicillanic acid.

7β-[D-2-(6,7-Dihydroxy-2-oxo-2H-1-benzopyran-3-carboxamide)-2-(4-hydroxyphenyl)acetamide]-3-acetoxymethyl-3-cephem-4-carboxylic acid.

7β-[D-2-(6,7-Dihydroxy-2-oxo-2H-1-benzopyran-3-carboxamide)-2-(4-hydroxyphenyl)acetamide]-3-(1-methyl-5-tetrazolyl)thiomethyl-3-cephem-4-carboxylic acid.

7β-[D-2-(6,7-Dihydroxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid.

7β-[D-2-(6,7-Dihydroxy-2-oxo-2H-1-benzopyran-3-carboxamide)-2-(4-hydroxyphenyl)acetamide]-3-[5-carboxymethyl-2-(1,3,4-thiadiazolyl)]thiomethyl-3-cephem-4-carboxylic acid.

7β-[D-2-(6,7-Dihydroxy-2-oxo-2H-1-benzopyran-3-carboxamide)-2-(4-hydroxyphenyl)acetamide]-3-[5-carboxymethyl-2-(1,3,4-oxadiazolyl)]thiomethyl-3-cephem-4-carboxylic acid.

7β-[D-2-(6,7-Dihydroxy-2-oxo-2H-1-benzopyran-3-carboxamide)-2-(4-hydroxyphenyl)acetamide]-3-(1-sulfomethyl-5-tetrazolyl)thiomethyl-3-cephem-4-carboxylic acid.

6β-[D-2-(7,8-Diacetoxy-2-oxo-2H-1-benzopyran-3-carboxamide)-2-(4-hydroxyphenyl)acetamide]penicillanic acid.

7β-[D-2-(7,8-Diacetoxy-2-oxo-2H-1-benzopyran-3-carboxamide)-2-phenylacetamide]-3-acetoxymethyl-3-cephem-4-carboxylic acid.

7β-[D-2-(7,8-Diacetoxy-2-oxo-2H-1-benzopyran-3-carboxamide)-2-(4-hydroxyphenyl)acetamide]-3-(1-methyl-5-tetrazolyl)thiomethyl-3-cephem-4-carboxylic acid.

7β-[D-2-(7,8-Dihydroxy-2-oxo-2H-1-benzopyran-3-carboxamide)-2-(4-hydroxyphenyl)acetamide]-3-acetoxymethyl-3-cephem-4-carboxylic acid.

7β-[D-2-(7,8-Dihydroxy-2-oxo-2H-1-benzopyran-3-carboxamide)-2-(4-hydroxyphenyl)acetamide]-7α-methoxy-3-acetoxymethyl-3-cephem-4-carboxylic acid.

7β-[D-2-(7,8-Dihydroxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid.

7β-[D-2-(7,8-Dihydroxy-2-oxo-2H-1-benzopyran-3-carboxamide)-2-(4-hydroxyphenyl)acetamide]-7α-methoxy-3-(1-carboxymethyl-5-tetrazolyl)-thiomethyl-3-cephem-4-carboxylic acid.

7β-[D-2-(7,8-Dihydroxy-2-oxo-2H-1-benzopyran-3-carboxamide)-2-(4-hydroxyphenyl)acetamide]-3-(1-sulfomethyl-3-carboxamide)-2-(4-hydroxyphenyl)acetamide]-3-(1-sulfomethyl-5-tetrazolyl)thiomethyl-3-cephem-4-carboxylic acid.

7β-[D-2-(7,8-Dihydroxy-2-oxo-2H-1-benzopyran-3-carboxamide)-2-(4-hydroxyphenyl)acetamide]-3-[5-carboxymethyl-2-(1,3,4-thiadiazolyl)]thiomethyl-3-cephem-4-carboxylic acid.

7β-[D-2-(7,8-Dihydroxy-2-oxo-2H-1-benzopyran-3-carboxamide)-2-(4-hydroxyphenyl)acetamide]-3-[5-carboxymethyl-2-(1,3,4-oxadiazolyl)]thiomethyl-3-cephem-4-carboxylic acid.

6β-[D-2-(6,7-Diacetoxy-2-oxo-2H-1-benzothiopyran-3-carboxamide)-2-phenylacetamide]penicillanic acid.

7β-[D-2-(6,7-Diacetoxy-2-oxo-2H-1-benzothiopyran-3-carboxamide)-2-(4-hydroxyphenyl)acetamide]-3-(1-methyl-5-tetrazolyl)thiomethyl-3-cephem-4-carboxylic acid.

7β-[D-2-(6,7-Diacetoxy-2-oxo-2H-1-benzothiopyran-3-carboxamide)-2-(4-hydroxyphenyl)acetamide]-3-(1-carboxymethyl-5-tetrazolyl)thiomethyl-3-cephem-4-carboxylic acid.

7β-[D-2-(6,7-Dihydroxy-2-oxo-2H-1-benzothiopyran-3-carboxamide)-2-(4-hydroxyphenyl)acetamide]-3-(1-carboxymethyl-5-tetrazolyl)thiomethyl-3-cephem-4-carboxylic acid.

7β-[D-2-(7,8-Dihydroxy-2-oxo-2H-1-benzothiopyran-3-carboxamide)-2-(4-hydroxyphenyl)acetamide]-3-(1-carboxymethyl-5-tetrazolyl)thiomethyl-3-cephem-4-carboxylic acid.

7β-[D-2-(6,7-Diacetoxy-1,2,-dihydro-2-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

7β-[D-2-(6,7-Diacetoxy-1,2-dihydro-2-oxoquinoline-3-carboxamide)-2-(4-hydroxyphenyl)acetamide]-3-(1-carboxymethyl-5-tetrazolyl)thiomethyl-3-cephem-4-carboxylic acid.

7β-[D-2-(6,7-Dihydroxy-1,2-dihydro-2-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

7β-[D-2-(7,8-Dihydroxy-1,2-dihydro-2-oxoquinoline-3-carboxamide)-2-phenylacetamide]-3-(1-sulfomethyl-5-tetrazolyl)thiomethyl-3-cephem-4-carboxylic acid.

7β-[D-2-(6,7-Diacetoxy-1-methyl-1,2-dihydro-2-oxoquinoline-3-carboxamide)-2-(4-hydroxyphenyl)acetamide]-3-acetoxymethyl-3-cephem-4-carboxylic acid.

6β-[D-2-(6,7-Dihydroxy-1,2-dihydro-2-oxoquinoline-3-carboxamide)-2-phenylacetamide]penicillanic acid.

7β-[D-2-(6-Acetoxy-7-hydroxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid.

7β-[D-2-(6-Acetoxy-7-hydroxy-2-oxoquinoline-3-carboxamide)-2-(4-hydroxyphenyl)acetamide]-3-(1-carboxymethyl-5-tetrazolyl)thiomethyl-3-cephem-4-carboxylic acid.

7β-[D-2-(6,7-Dihydroxy-2-oxo-2H-1-benzopyran-3-carboxamide)-2-(4-hydroxyphenyl)acetamide]-7α-methoxy-3-(1-carboxymethyl-5-tetrazolyl)thiomethyl-3-cephem-4-carboxylic acid.

6β-[D-2-(6,7-Dihydroxy-2-oxo-2H-1-benzopyran-3-carboxamide)-2-(4-hydroxyphenyl)acetamide]-penicillanic acid pivaloyloxymethyl ester.

The compounds (I-1) and (I-2) of this invention have outstanding antibacterial activity, particularly for *Kleb. pneumoniae* and *Pseud. aeruginosa*.

The acute toxicity values [$LD_{50}$ (mouse, oral)] of the compounds of this invention are higher than 4 g/kg in the case of 7β-[D-2-(6,7-dihydroxy-4-oxo-4H-1-benzothiopyran-3-carboxamide)-2-(4-hydroxyphenyl)acetamide]-3-(1-carboxymethyl-5-tetrazolyl)thiomethyl-3-cephem-4-carboxylic acid and 7β-[D-2-(6,7-diacetoxy-1-ethyl-1,4-dihydro-4-oxoquinoline-3-carboxamide)-2-(4-hydroxyphenyl)acetamide]-3-(1-carboxymethyl-5-tetrazolyl)thiomethyl-3-cephem-4-carboxylic acid, as well as 7β-[D-2-(6,7-dihydroxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid and 7β-[D-2-(6,7-dihydroxy-2-oxo-2H-1-benzothiopyran-3-carboxamide)-2-(4-hydroxyphenyl)acetamide]-3-(1-carboxymethyl-5-tetrazolyl)thiomethyl-3-cephem-4-carboxylic acid.

When used as an antibacterial composition, the compounds of this invention should be administered usually at a dosage of 2 to 300 mg/kg/day, preferably 10 to 100 mg/kg/day. This drug is administered orally in the form of powder, granules, tablets, capsules, syrup, etc. or parenterally in the form of injections, suppositories, etc. These pharmaceutical preparations are manufactured in the usual way using common carriers which are pharmaceutically acceptable.

The following examples illustrate this invention, but are not to be construed as limiting the scope thereof.

EXAMPLE 1

7β-[D-2-(6,7-Diacetoxy-1,4-dihydro-4-oxoquinoline-3-carboxamide)-2-(4-hydroxyphenyl)acetamide]-3-(1-carboxymethyl-5-tetrazolyl)thiomethyl-3-cephem-4-carboxylic acid.

6,7-Diacetoxy-1,4-dihydro-4-oxoquinoline-3-carboxylic acid (70 mg) was heated under reflux for 2 hours in thionyl chloride (2 mL), and then the solvent was evaporated. To the residue was added benzene (30 mL). Benzene was evaporated and the residue was vacuum dried to give 6,7-diacetoxy-1,4-dihydro-4-oxoquinoline-3-carbonyl chloride.

7β-[D-2-Amino-2-(4-hydroxyphenyl)acetamide]-3-(carboxymethyl-5-tetrazolyl)thiomethyl-3-cephem-4-carboxylic acid (112 mg) was suspended in tetrahydrofuran (20 mL), to which N,O-bis(trimethylsilyl)acetamide (270 μL) was added. The mixture was stirred at room temperature for 8 hours, and then cooled with ice. To this mixture was added tetrahydrofuran solution (10 mL) of the whole amount of the aforesaid carbonyl chloride, and the mixture was stirred for 2 hours with ice cooling. The reaction mixture was concentrated to about 5 mL. The concentrated solution was added dropwise to 0.2N hydrochloric acid (30 mL) with stirring and ice cooling. The separated solids were filtered off, followed by water washing and drying. Thus, the desired compound (110 mg) was obtained.

Infrared absorption spectrum ($cm^{-1}$, nujol): 1760, 1620

NMR spectrum (δ, DMSO-$d_6$): 2.38 (6H, s), 3.52–3.70 (2H, m), 5.00 (1H, d, J=5 Hz), 5.23 (2H, s), 5.67–5.82 (2H, m), 6.75 (2H, d, J=9 Hz), 7.30 (2H, d, J=9 Hz), 8.03 (1H, s), 8.15 (1H, s), 8.83 (1H, s)

EXAMPLE 2

6β-[D-2-(6,7-Diacetoxy-1-ethyl-1,4-dihydro-4-oxoquinoline-3-carboxamide)-2-phenylacetamide]penicillanic acid.

A mixture of 6,7-diacetoxy-1-ethyl-1,4-dihydro-4-oxoquinoline-3-caroxylic acid (60 mg), thionyl chloride (40 μL), and dimethylformamide (one drop) was heated under reflux for 3 hours in benzene (40 mL), and then the solvent was evaporated. To the residue was added benzene (20 mL). Benzene was evaporated and the residue was vacuum dried to give 6,7-diacetoxy-1-ethyl-1,4-dihydro-4-oxoquinoline-3-carbonyl chloride.

Ampicillin trihydrate (70 mg) was suspended in tetrahydrofuran (20 mL), to which N,O-bis(trimethylsilyl)acetamide (230 μL) was added. The mixture was stirred at room temperature for 3 hours, and then cooled with ice. To this reaction mixture was added tetrahydrofuran solution (10 mL) of the whole amount of the aforesaid carbonyl chloride, and the mixture was stirred for 1 hour with ice cooling and then 2 hours at room temperature. The reaction mixture was concentrated to about 5 mL. The concentrated solution was added dropwise to 0.2N hydrochloric acid (45 mL) with stirring and ice cooling. The separated solids were filtered off, followed by water washing and drying. Thus, the desired compound (60 mg) was obtained.

Infrared absorption spectrum (cm$^{-1}$, nujol): 1770, 1640

NMR spectrum (δ, DMSO-d$_6$): 1.39 (3H, t, J=6 Hz), 1.42 (3H, s), 1.60 (3H, s), 2.36 (3H, s), 2.37 (3H, s), 4.20 (1H, s), 4.47 (2H, q, J=6 Hz), 5.35–5.64 (2H, m), 5.96 (1H, d, J=7 Hz), 7.16–7.55 (5H, m), 7.92 (1H, s), 8.18 (1H, s), 8.84 (1H, s)

EXAMPLE 3

7β-[D-2-(6,7-Diacetoxy-1-ethyl-1,4-dihydro-4-oxoquinoline-3-carboxamide)-2-(4-hydroxyphenyl)acetamide]-3-acetoxymethyl-3-cephem-4-carboxylic acid.

7β-[D-2-Amino-2-(hydroxyphenyl)acetamide]-3-acetoxymethyl-3-cephem-4-carboxylic acid (76 mg) was reacted with 6,7-diacetoxy-1-ethyl-1,4-dihydro-4-oxoquinoline-3-carbonyl chloride as in Example 2 to give the desired compound (90 mg).

Infrared absorption spectrum (cm$^{-1}$, nujol): 1770, 1650

NMR spectrum (δ, DMSO-d$_6$): 1.39 (3H, t, J=6 Hz), 2.02 (3H, s), 2.36 (3H, s), 2.37 (3H, s), 4.47 (2H, q, J=6 Hz), 4.66 (1H, d, J=13 Hz), 4.99 (1H, d, J=13 Hz), 5.02 (1H, d, J=5 Hz), 5.62–5.83 (2H, m), 6.72 (2H, d, J=9 Hz), 7.29 (2H, d, J=9 Hz), 7.91 (1H, s), 8.18 (1H, s) 8.85 (1H, s)

EXAMPLE 4

7β-[D-2-(6,7-Diacetoxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

7β-[D-2-Amino-2-(4-hydroxydiphenyl)acetamide]-3-[5-methyl-2-(1,3,4-thiadiazolyl)thiomethyl]-3-cephem-4-carboxylic acid (148 mg) was reacted with 6,7-diacetoxy-1-ethyl-1,4-dihydro-4-oxoquinoline-3-carbonyl chloride as in Example 2 to give the desired compound (218 mg).

Infrared absorption spectrum (cm$^{-1}$, nujol): 1770, 1650

NMR spectrum (δ, DMSO-d$_6$): 1.32 (3H, t, J=6 Hz), 2.30 (6H, s), 2.60 (3H, s), 4.13 (1H, d, J=14 Hz), 4.45 (1H, d, J=14 Hz), 4.48 (2H, q, J=6 Hz), 4.97 (1H, d, J=5 Hz), 5.57–5.76 (2H, m), 6.65 (2H, d, J=9 Hz), 7.23 (2H, d, J=9 Hz), 7.86 (1H, s), 8.11 (1H, s), 8.80 (1H, s)

EXAMPLE 5

7β-[D-2-(6,7-Diacetoxy-1-ethyl-1,4-dihydro-4-oxoquinoline-3-carboxamide)-2-(4-hydroxyphenyl)acetamide]-3-(1-carboxymethyl-5-tetrazolyl)thiomethyl-3-cephem-4-carboxylic acid.

7β-[D-2-Amino-2-(4-hydroxyphenyl)acetamide]-3-(1-carboxymethyl-5-tetrazolyl)thiomethyl-3-cephem-4-carboxylic acid (94 mg) was reacted with 6,7-diacetoxy-1-ethyl-1,4-dihydro-4-oxoquinoline-3-carbonyl chloride as in Example 2 to give the desired compound (80 mg).

Infrared absorption spectrum (cm$^{-1}$, nujol): 1760, 1640

NMR spectrum (δ, DMSO-d$_6$): 1.36 (3H, t, J=6 Hz), 2.35 (3H, s), 2.36 (3H, s), 4.43 (2H, q, J=6 Hz), 4.96 (1H, d, J=5 Hz), 5.25 (2H, s), 5.62–5.78 (2H, m), 6.70 (2H, d, J=9 Hz), 7.25 (2H, d, J=9 Hz), 7.90 (1H, s), 8.15 (1H, s), 8.83 (1H, s)

EXAMPLE 6

7β-[D-2-(6,7-Dihydroxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

7β-[D-2-(6,7-Diacetoxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid (81 mg) obtained in Example 4 was suspended in methylene chloride (10 mL). Dihydropyran (260 mg) and p-toluenesulfonic acid (a catalytic amount) were added. After stirring for 2 hours at room temperature, the solvent was evaporated. To the residue were added ethanol-water (1:1, 9 mL) and sodium hydrogen carbonate (40 mg). After stirring for 2 hours at 50° C., the reaction mixture was concentrated to about 5 mL, and then 0.25N hydrochloric acid (20 mL) was added with ice cooling. The separated solids were filtered off and then dissolved in methanol (5 mL). The solution was stirred overnight after adding p-toluenesulfonic acid (a catalytic amount). Most of methanol was distilled off and ethyl ether was added. Separated solids were filtered off to yield the desired compound (50 mg).

Infrared absorption spectrum (cm$^{-1}$, nujol): 1760, 1640

NMR spectrum (δ, DMSO-d$_6$): 1.39 (3H, t, J=7 Hz), 2.70 (3H, s), 4.46 (2H, q, J=7 Hz), 5.02 (1H, d, J=5 Hz), 5.62–5.80 (2H, m), 6.72 (2H, d, J=9 Hz), 7.10 (1H, s), 7.26 (2H, d, J=9 Hz), 7.63 (1H, s), 8.62 (1H, s)

EXAMPLE 7

7β-[D-2-(6,7-Diacetoxy-4-oxo-4H-1-benzothiopyran-3-carboxamide)-2-(4-hydroxyphenyl)acetamide]-3-(1-methyl-5-tetrazolyl)thiomethyl-3-cephem-4-carboxylic acid.

A mixture of 6,7-diacetoxy-4-oxo-4H-1-benzothiopyran-3-carboxylic acid (50 mg), thionyl chloride (40 μL), and dimethylformamide (one drop) was heated under reflux for 2 hours in benzene (20 mL), and then the solvent was distilled off. To the residue was added benzene (20 mL). Benzene was evaporated again and the residue was vacuum dried to give 6,7-diacetoxy-4-oxo-4H-1-benzothiopyran-3-carbonyl chloride.

7β-[D-2-Amino-2-(4-hydroxyphenyl)acetamide]-3-(1-methyl-5-tetrazolyl)thiomethyl-3-cephem-4-carboxylic acid (65 mg) was suspended in tetrahydrofuran (20 mL), to which N,O-bis(trimethylsilyl)acetamide (150 μL) was added. The reactants were stirred at room temperature for 2 hours, and then cooled with ice. To this reaction mixture was added the aforesaid carbonyl chloride (whole amount) and tetrahydrofuran (15 mL), and the mixture was stirred for 3 hours with ice cooling. The reaction mixture was concentrated to about 5 mL. The concentrated solution was added dropwise to 0.2N hydrochloric acid (20 mL) with stirring and ice cooling. The separated solids were filtered off, followed by water washing and drying. Thus, the desired compound (55 mg) was obtained.

Infrared absorption spectrum (cm$^{-1}$, nujol): 1770, 1640

NMR spectrum (δ, DMSO-d$_6$): 2.35 (6H, s), 3.92 (3H, s), 4.99 (1H, d, J=5 Hz), 5.60–5.81 (2H, m), 6.71 (2H, d, J=9 Hz), 7.25 (2H, d, J=9 Hz), 8.09 (1H, s), 8.38 (1H, s), 9.51 (1H, s)

EXAMPLE 8

7β-[D-2-(6,7-Diacetoxy-4-oxo-4H-1-benzothiopyran-3-carboxamide)-2-(4-hydroxyphenyl)acetamide]-3-(1-carboxymethyl-5-tetrazolyl)thiomethyl-3-cephem-4-carboxylic acid.

7β-[D-2-Amino-2-(4-hydroxyphenyl)acetamide]-3-(1-carboxymethyl-5-tetrazolyl)thiomethyl-3-cephem-4-carboxylic acid (113 mg) was reacted with 6,7-diacetoxy-4-oxo-4H-1-benzothiopyran-3-carbonyl chloride as in Example 7 to give the desired compound (136 mg).

Infrared absorption spectrum (cm$^{-1}$, nujol): 1750, 1640

NMR spectrum (δ, DMSO-d$_6$): 2.36 (6H, s), 3.46–3.75 (2H, m), 4.20 (1H, d, J=14 Hz), 4.46 (1H, d, J=14 Hz), 4.98 (1H, d, J=5 Hz), 5.30 (2H, s), 5.65–5.82 (2H, m), 6.72 (2H, d, J=9 Hz), 7.30 (2H, d, J=9 Hz), 8.10 (1H, s), 8.40 (1H, s), 9.55 (1H, s)

EXAMPLE 9

7β-[D-2-(6,7-Dihydroxy-4-oxo-4H-1-benzothiopyran-3-carboxamide)-2-(4-hydroxyphenyl)acetamide]-3-(1-methyl-5-tetrazolyl)thiomethyl-3-cephem-4-carboxylic acid.

6,7-Dihydroxy-4-oxo-4H-1-benzothiopyran-3-carboxylic acid (100 mg) was heated under reflux for 2 hours in thionyl chloride (5 mL), and then the thionyl chloride was distilled off. To the residue was added benzene (20 mL). Benzene was distilled off again and the residue was vacuum dried to give 6,7-dihydro-4-oxo-4H-1-benzothiopyran-3-carbonyl chloride.

7β-[D-2-Amino-2-(4-hydroxyphenyl)acetamide]-3-(1-methyl-5-tetrazolyl)thiomethyl-3-cephem-4-carboxylic acid (174 mg) was suspended in tetrahydrofuran (20 mL), to which N,O-bis(trimethylsilyl)acetamide (420 μL) was added. The mixture was stirred at room temperature for 5 hours, and then cooled with ice. To this reaction product was added the aforesaid carbonyl chloride (whole amount) in tetrahydrofuran (10 mL). The reactants were stirred for 2 hours with ice cooling. The reaction mixture was concentrated to about 5 mL. The concentrated solution was added dropwise to 0.2N hydrochloric acid (20 mL) with stirring and ice cooling. The separated solids were filtered off, followed by water washing and drying. Thus, the desired compound (70 mg) was obtained.

Infrared absorption spectrum (cm$^{-1}$, nujol): 1770, 1640

NMR spectrum (δ, DMSO-d$_6$): 3.50 (1H, d, J=18 Hz), 3.72 (1H, d, J=18 Hz), 3.93 (3H, s), 4.20 (1H, d, J=14 Hz), 4.36 (1H, d, J=14 Hz), 5.02 (1H, d, J=5 Hz), 5.61–5.81 (2H, m), 6.75 (2H, d, J=9 Hz), 7.22 (1H, s), 7.25 (2H, d, J=9 Hz), 7.90 (1H, s), 9.32 (1H, s)

EXAMPLE 10

7β-[D-2-(6,7-Dihydroxy-4-oxo-4H-1-benzothiopyran-3-carboxamide)-2-(4-hydroxyphenyl)acetamide]-3-(1-carboxymethyl-5-tetrazolyl)thiomethyl-3-cephem-4-carboxylic acid.

7β-[D-2-(6,7-Diacetoxy-4-oxo-4H-1-benzothiopyran-3-carboxamide)-2-(4-hydroxyphenyl)acetamide]-3-(1-carboxymethyl-5-tetrazolyl)thiomethyl-3-cephem-4-carboxylic acid (60 mg) obtained in Example 8 was suspended in methylene chloride (6 mL). Dihydropyran (189 mg) and p-toluenesulfonic acid (in a catalytic amount) were added. After stirring for 2 hours at room temperature, the solvent was distilled off. To the residue were added ethanol-water (1:1, 9 mL) and sodium hydrogen carbonate (28 mg). After stirring for 1 hour at 50° C., the reaction mixture was concentrated to about 5 mL, and then 0.25N hydrochloric acid (20 mL) was added with ice cooling. The separated solids were filtered off and then dissolved in methanol (3 mL). The solution was stirred overnight after adding p-toluenesulfonic acid (a catalytic amount). Most of methanol was distilled off and ethyl ether was added. Separated solids were filtered off to yield the desired compound (22 mg).

Infrared absorption spectrum (cm$^{-1}$, nujol): 1750, 1640

NMR spectrum (δ, DMSO-d$_6$): 4.99 (1H, d, J=5 Hz), 5.30 (2H, s), 5.61–5.75 (2H, m), 6.72 (2H, d, J=9 Hz), 7.20 (1H, s), 7.23 (2H, d, J=9 Hz), 7.89 (1H, s), 9.31 (1H, s)

EXAMPLE 11

7β-[D-2-(6,7-Diacetoxy-4-oxo-4H-1-benzothiopyran-3-carboxamide)-2-(4-hydroxyphenyl)acetamide]-7α-methoxy-3-acetoxymethyl-3-cephem-4-carboxylic acid.

7β-[D-2-Amino-2-(4-hydroxyphenyl)acetamide]-7α-methoxy-3-acetoxymethyl-3-cephem-4-carboxylic acid trifluoroacetate (65 mg) was suspended in tetrahydrofuran (15 mL). N,O-bis(trimethylsilyl)acetamide (120 μL) was added with stirring at room temperature. After stirring for 3 hours, the solution was cooled with ice. The carbonyl chloride (whole amount) prepared as in Example 7 from 37 mg of 6,7-diacetoxy-4-oxo-4H-1-benzothiopyran was added together with tetrahydrofuran (10 mL). The mixture was stirred with ice cooling for 2 hours. The reaction mixture was concentrated to about 1 mL and then added dropwise into 0.25N hydrochloric acid (40 mL) with stirring and ice cooling. Separated solids were filtered off and washed with water. The solids thus obtained were dissolved in ethyl acetate (60 mL). After removal of the insoluble material, the solution was washed with brine. The ethyl acetate layer was concentrated to about 5 mL. The concentrated solution was added dropwise to ethyl ether (100 mL) with stirring. Separated solids were filtered off and washed with ethyl ether to yield the desired compound (36 mg).

Infrared absorption spectrum (cm$^{-1}$, nujol): 1780, 1650, 1610

NMR spectrum (δ, DMSO-d$_6$): 2.00 (3H, s), 2.35 (6H, s), 3.43 (3H, s), 4.62 (1H, d, J=13 Hz), 4.94 (1H, d, J=13 Hz), 5.12 (1H, s), 5.69 (1H, d, J=6 Hz), 6.76 (2H, d, J=8 Hz), 7.35 (2H, d, J=8 Hz), 8.15 (1H, s), 8.38 (1H, s), 9.57 (1H, s)

EXAMPLE 12

7β-[D-2-(6-Acetoxy-7-hydroxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid sodium salt.

7β-[D-2-(6,7-Diacetoxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid (100 mg) obtained in Example 4 was dissolved in a mixture of tetrahydrofuran (5 mL) and methanol (5 mL). 0.5M Methanol solution (0.3 mL) of sodium 2-ethylhexanoate was added with stirring, and the solution was stirred for 2 hours and 40 minutes at room temperature. Then, ethyl ether (30 mL) was added, and separated solids were filtered off to yield the desired compound (70 mg).

Infrared absorption spectrum (cm$^{-1}$, nujol): 1760, 1650, 1600

NMR spectrum (δ, DMSO-d$_6$): 1.32 (3H, t, J=6 Hz), 2.30 (3H, s), 2.65 (3H, s), 3.26 (2H, d, J=17 Hz), 3.56 (2H, d, J=17 Hz), 4.35 (2H, d, J=13 Hz), 4.55 (2H, d, J=13 Hz), 4.48 (2H, q, J=6 Hz), 4.92 (1H, d, J=5 Hz), 5.40–5.65 (2H, m), 5.75 (1H, d, J=8 Hz), 6.71 (2H, d, J=8 Hz), 7.26 (2H, d, J=8 Hz), 7.21 (1H, s), 7.90 (1H, s), 8.60, (1H, s)

EXAMPLE 13

7β-[D-2-(6-Acetoxy-7-hydroxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid pivaloyloxymethyl ester.

7β-[D-2-(6-Acetoxy-7-hydroxy-1-ethyl-1,4-dihydro-4-oxoquinoline-3-carboxamide)-2-(4-hydroxyphenyl)acetamide]-3-[5-methyl-2-(1,3,4-thiadiazolyl)]thiomethyl-3-cephem-4-carboxylic acid sodium salt (42 mg) obtained in Example 12 was dissolved in dimethylformamide (1 mL) under argon. Sodium iodide (catalytic amount) and chloromethylpivalate (15 μL) were added, followed by stirring for 5.5 hours at room temperature. Additional chloromethylpivalate (30 μL) was added, followed by stirring for 2 days. The reaction mixture was added dropwise to cold water (50 mL). Separated crystals were filtered off and dissolved in ethyl acetate (100 mL). After removal of the insolubles material by filtration, the solution was washed with 5% aq. solution of sodium acetate (50 mL×2), with water (50 mL×2), and brine (50 mL×1) in the order listed. The washed solution was dried over magnesium sulfate, and the solvent was distilled off. The residue was washed with ethyl ether, and the desired compound (14 mg) was obtained through filtration.

Infrared absorption spectrum (cm$^{-1}$, nujol): 1760, 1650, 1610, 1600

NMR spectrum (δ, DMSO-d$_6$): 1.15 (9H, s), 2.31 (3H, s), 2.68 (3H, s), 5.05 (1H, d, J=5 Hz), 5.60–6.05 (4H, m), 6.73 (2H, d, J=8 Hz), 7.21 (1H, s), 7.25 (2H, d, J=8 Hz), 7.95 (1H, s), 8.75 (1H, s)

EXAMPLE 14

6β-[D-2-(6,7-Diacetoxy-2-oxo-2H-1-benzopyran-3-carboxamide)-2-phenylacetamide]penicillanic acid.

A mixture of 6,7-diacetoxy-2-oxo-2H-1-benzopyran-3-carboxylic acid (306 mg), thionyl chloride (80 μL), dimethyl formamide (one drop), and benzene (15 mL) was refluxed for 1 hour. After cooling to room temperature, hexane (10 mL) was added. Solids were filtered off to give 6,7-diacetoxy-2-oxo-2H-1-benzopyran-3-carbonyl chloride (286 mg).

Ampicillin trihydrate (161 mg) was suspended in ethyl acetate (4 mL), and N,O-bis(trimethylsilyl)acetamide (395 μL) was added, followed by stirring for 10 minutes at room temperature. After cooling to 5° C., the above-mentioned carbonyl chloride (130 mg) was added, followed by stirring for 2 hours at about 0° C. Ethyl acetate (100 mL) was added. The reaction mixture was washed with 0.5N hydrochloric acid (20 mL×1), water (20 mL×2), and brine (20 mL×2). The solution was dried over magnesium sulfate and the solvent was distilled off. The residue was solidified with ethyl ether and washed with 2% tetrahydrofuran ethyl ether to yield the desired compound (189 mg).

Infrared absorption spectrum (cm$^{-1}$, nujol): 1770–1790, 1725, 1710, 1645–1660, 1610, 1570

NMR spectrum (δ, DMSO-d$_6$): 1.41 (3H, s), 1.55 (3H, s), 2.33 (6H, s), 4.20 (1H, s), 5.39 (1H, d, J=4 Hz), 5.55 (1H, dd, J=8 Hz, 4 Hz), 5.92 (1H, d, J=8 Hz), 7.2–7.4 (5H, m), 7.58 (1H, s), 7.93 (1H, s), 8.73 (1H, s)

EXAMPLE 15

7β-[D-2-(6,7-Diacetoxy-2-oxo-2H-1-benzopyran-3-carboxamide)-2-(4-hydroxyphenyl)acetamide]-3-acetoxymethyl-3-cephem-4-carboxylic acid.

7β-[D-2-Amino-2-(4-hydroxyphenyl)acetamide]-3-acetoxymethyl-3-cephem-4-carboxylic acid (169 mg) was suspended in ethyl acetate (4 mL) at 0° C. N,O-Bis(trimethylsilyl)acetamide (395 μL) was added with stirring. After stirring for 10 minutes at 0° C., 6,7-diacetoxy-2-oxo-2H-1-benzopyran-3-carbonyl chloride (130 mg) was added, followed by stirring for 1 hour at room temperature. Ethyl acetate (100 mL) was added. The reaction mixture was washed with 0.5N hydrochloric acid (20 mL×1), with water (20 mL×2), and with brine (20 mL×2). After drying over magnesium sulfate, the solvent was distilled off. The residue was dissolved in acetone (10 mL), and the solution was allowed to stand for 24 hours at room temperature. Acetone was distilled off. The residue was suspended in ethyl ether and filtered off. The solid was washed with 2% tetrahydrofuran-ethyl ether to yield the desired compound (213 mg).

Infrared absorption spectrum (cm$^{-1}$, nujol): 1760–1790, 1720, 1705, 1655–1640, 1610

NMR spectrum (δ, DMSO-d$_6$): 2.01 (3H, s), 2.32 (6H, s), 4.64 (2H, d, J=13 Hz), 4.92 (2H, d, J=13 Hz), 5.02 (1H, d, J=5 Hz), 5.6–5.9 (2H, m), 6.71 (2H, d, J=8 Hz), 7.24 (2H, d, J=8 Hz), 7.57 (1H, s), 7.92 (1H, s), 8.83 (1H, s)

EXAMPLE 16

7β-[D-2-(6,7-Diacetoxy-2-oxo-2H-1-benzopyran-3-carboxamide)-2-(4-hydroxyphenyl)acetamide]-3-(carboxymethyl-5-tetrazolyl)thiomethyl-3-cephem-4-carboxylic acid.

7β-[D-2-Amino-2-(4-hydroxyphenyl)acetamide]-3-(1-carboxymethyl-5-tetrazolyl)thiomethyl-3-cephem-4-carboxylic acid trifuloroacetate (320 mg) was suspended in tetrahydrofuran (20 mL) at 0° C. N,O-Bis(trimethylsilyl)acetamide (1.2 mL) was added with stirring. After stirring for 10 minutes at 0° C., 6,7- diacetoxy-2-oxo-2H-1-benzopyran-3-carbonyl chloride (162 mg) was added. 0.2N hydrochloric acid (50 mL) was added, and extraction was carried out twice with ethyl acetate (100 mL). The organic layer was washed with water (50 mL×2), and with brine (20 mL×2). After drying over magnesium sulfate, the solvent was distilled off. The residue was solidified with ethyl ether and the desired compound (270 mg) was filtered off.

Infrared absorption spectrum (cm$^{-1}$, nujol): 1780–1760, 1700, 1660, 1610

NMR spectrum ($\delta$, DMSO-d$_6$): 2.54 (6H, s), 3.51 (1H, d, J=18 Hz), 3.66 (1H, d, J=18 Hz), 4.18 (1H, d, J=14 Hz), 4.42 (1H, d, J=14 Hz), 4.98 (1H, d, J=5 Hz), 5.28 (2H, s), 5.57–5.90 (2H, m), 6.71 (2H, d, J=9 Hz), 7.23 (2H, d, J=9 Hz), 7.58 (1H, s), 7.95 (1H, s)

EXAMPLE 17

6$\beta$-[D-2-(6,7-Dihydroxy-2-oxo-2H-1-benzopyran-3-carboxamide)-2-phenylacetamide]penicillanic acid.

6$\beta$-[D-2-(6,7-Diacetoxy-2-oxo-2H-1-benzopyran-3-carboxamide)-2-phenylacetamide)penicillanic acid (30 mg) which was obtained in Example 14 was dissolved in dimethylsulfoxide (300 $\mu$L). To this solution was added 0.5M aq. solution of sodium hydrogen carbonate (283 $\mu$L), and the solution was stirred for 24 hours at room temperature. The reaction mixture was diluted with ethyl acetate (100 mL). The diluted solution was washed with 0.5N hydrochloric acid (20 mL×1), with water (20 mL×3), and with brine (20 mL×2). After drying over magnesium sulfate, the solvent was distilled off. The residue was solidified with ethyl ether and the desired compound (27 mg) was obtained.

Infrared absorption spectrum (cm$^{-1}$, nujol): 1775, 1755, 1720, 1700, 1650–1690

NMR spectrum ($\delta$, DMSO-d$_6$): 1.41 (3H, s), 1.55 (3H, s), 4.20 (1H, s), 5.39 (1H, d, J=4 Hz), 5.55 (1H, dd, J=8 Hz, 4 Hz), 5.90 (1H, d, J=8 Hz), 6.75 (1H, s), 7.21 (1H, s), 7.2–7.55 (5H, m), 8.72 (1H, s)

EXAMPLE 18

6$\beta$-[D-2-(6,7-Dihydroxy-2-oxo-2H-1-benzopyran-3-carboxamide)-2-(4-hydroxyphenyl)acetamide]penicillanic acid.

A mixture of 6,7-dihydroxy-2-oxo-2H-1-benzopyran-3-carboxylic acid (110 mg), thionyl chloride (5 mL), and dimethylformamide (one drop) was stirred for 2 hours at room temperature. The excess thionyl chloride was distilled off in vacuo. Benzene (20 mL) was added, followed by vacuum distillation and vacuum drying, to yield 6,7-dihydroxy-2-oxo-2H-1-benzopyran-3-carbonyl chloride.

Amoxicillin trihydrate (210 mg) was suspended in tetrahydrofuran (20 mL), to which N,O-bis(trimethylsilyl)acetamide (0.8 mL) was added with stirring and ice cooling. The solution was stirred for 10 minutes at the same temperature. To this solution was added the above-mentioned carbonyl chloride (whole amount) suspended in tetrahydrofuran. After stirring for 3 hours at about 0° C., tetrahydrofuran was distilled off. To the residue was added 1N hydrochloric acid (40 mL). Extraction was carried out with ethyl acetate (200 mL), followed by washing with water (40 mL×2) and with brine (40 mL×2). After drying over magnesium sulfate, the solvent was distilled off. The residue was dissolved in ethyl acetate (50 mL), and the insoluble material was filtered off. The solvent was distilled off again. The residue was dissolved in tetrahydrofuran (4 mL), to which ethyl ether (80 mL) was added dropwise with stirring. The precipitates were filtered off to yield the desired compound (95 mg).

Infrared absorption spectrum (cm$^{-1}$, nujol): 1760, 1700, 1685, 1615

NMR spectrum ($\delta$, DMSO-d$_6$): 1.42 (3H, s), 1.58 (3H, s), 4.20 (1H, s), 5.40 (1H, d, J=5 Hz), 5.57 (1H, dd, J=8 Hz, 5 Hz), 5.78 (1H, d, J=8 Hz), 6.70 (2H, d, J=9 Hz), 6.84 (1H, s), 7.21 (1H, s), 7.22 (2H, d, J=9 Hz), 8.73 (1H, s)

EXAMPLE 19

6$\beta$-[D-2-(6-Hydroxy-7-sodiooxy-2-oxo-2H-1-benzopyran-3-carboxamide)-2-(4-hydroxyphenyl)acetamide]-penicillanic acid sodium salt.

6$\beta$-[D-2-(6,7-Dihydroxy-2-oxo-2H-1-benzopyran-3-carboxamide)-2-(4-hydroxyphenyl)acetamide]penicillanic acid (47 mg) obtained in Example 18 was dissolved in methanol (5 mL) with stirring. 1M Methanol solution of sodium acetate (0.25 mL) was added and the solution was stirred for 30 minutes at room temperature. The methanol was distilled off The residual solid was suspended in ethanol (3 mL) and filtered off. Then the solid was washed with ethyl ether to yield the desired compound (43 mg).

Infrared absorption spectrum (cm$^{-1}$, nujol): 1760, 1700, 1670, 1610

NMR spectrum ($\delta$, DMSO-d$_6$): 1.40 (3H, s), 1.54 (3H, s), 3.85 (1H, s), 5.25 (1H, d, J=4 Hz), 5.39 (1H, dd, J=8 Hz, 5 Hz), 5.76 (1H, d, J=8 Hz), 6.01 (1H, s), 6.64 (1H, s), 6.70 (2H, d, J=9 Hz), 7.21 (2H, d, J=9 Hz), 8.22 (1H, s)

EXAMPLE 20

7$\beta$-[D-2-(6,7-Dihydroxy-2-oxo-2H-1-benzopyran-3-carboxamide)-2-(4-hydroxyphenyl)acetamide]-3-(1-methyl-5-tetrazolyl)thiomethyl-3-cephem-4-carboxylic acid.

7$\beta$-[D-2-Amino-2-(4-hydroxyphenyl)acetamide]-3-(1-methyl-5-tetrazolyl)thiomethyl-3-cephem-4-carboxylic acid (270 mg) was suspended in tetrahydrofuran (40 mL), to which N,O-bis(trimethylsilyl)acetamide (0.5 mL) was added with stirring and ice cooling. The solution was stirred for 10 minutes at the same cooled temperature. To this solution was added 6,7-dihydroxy-2-oxo-2H-1-benzopyran-3-carbonyl chloride (120 mg) suspended in tetrahydrofuran (20 mL). After stirring for 1 hour at about 0° C. for a further 5 hours at room temperature, tetrahydrofuran was distilled off. To the residue was added 1N hydrochloric acid (40 mL) and extraction was carried out with ethyl acetate (200 mL). The extract was washed with water (40 mL×2) and with brine (40 mL×2). After drying over magnesium sulfate, the solvent was distilled off. The residue was solidified with 2% tetrahydrofuranethyl ether and then filtered off to yield the desired compound (141 mg).

Infrared absorption spectrum (cm$^{-1}$, nujol): 1770, 1700, 1620

NMR spectrum ($\delta$, DMSO-d$_6$): 3.55 (1H, d, J=16 Hz), 3.70 (1H, d, J=16 Hz), 3.94 (3H, s), 4.19 (1H, d, J=14 Hz), 4.37 (1H, d, J=14 Hz), 5.00 (1H, d, J=5 Hz), 5.57–5.82 (2H, m), 6.70 (2H, d, J=8 Hz), 6.83 (1H, s), 7.21 (1H, s), 7.22 (2H, d, J=8 Hz), 8.72 (1H, s)

EXAMPLE 21

7$\beta$-[D-2-(6,7-Dihydroxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid.

7β-[D-2-Amino-2-(4-hydroxyphenyl)acetamide]-3-(1-carboxymetyl-5-tetrazolyl)thiomethyl-3-cephem-4-carboxylic acid trifluoroacetate (320 mg) was suspended in tetrahydrofuran (20 mL), to which N,O-bis(trimethylsilyl)acetamide (0.65 mL) was added with stirring and ice cooling. The solution was stirred for 10 minutes. To this solution was added 6,7-dihydroxy-2-oxo-2H-1-benzopyran-3-carbonyl chloride (120 mg) suspended in tetrahydrofuran (20 mL). After stirring for 1 hour at about 0° C. and for a further 5 hours at room temperature, the reaction mixture was treated as in Example 20 to yield the desired compound (74 mg).

Infrared absorption spectrum (cm$^{-1}$, nujol): 1760, 1720, 1700, 1610

NMR spectrum (δ, DMSO-d$_6$): 3.51 (1H, d, J=17 Hz), 3.66 (1H, d, J=17 Hz), 4.18 (1H, d, J=14 Hz), 4.45 (1H, d, J=14 Hz), 4.97 (1H, d, J=5 Hz), 5.26 (2H, s), 5.57–5.84 (2H, m), 6.70 (2H, d, J=8 Hz), 6.82 (1H, s), 7.20 (1H, s), 7.24 (2H, d, J=8 Hz), 8.71 (1H, s)

EXAMPLE 22

6β-[D-2-(7,8-Diacetoxy-2-oxo-2H-1-benzopyran-3-carboxamide)-2-(4-hydroxyphenyl)acetamide]penicillanic acid.

A mixture of 7,8-diacetoxy-2-oxo-2H-1-benzopyran-3-carboxylic acid (612 mg), thionyl chloride (0.5 mL), dimethylformamide (one drop), and benzene (40 mL) was refluxed for 1 hour and then concentrated to about 10 mL. Hexane (20 mL) was added and the separated precipitates were filtered off, followed by vacuum drying, to yield 7,8-diacetoxy-2-oxo-2H-1-benzopyran-3-carbonyl chloride (600 mg).

Amoxicillin trihydrate (210 mg) was suspended in ethyl acetate (10 mL), to which N,O-bis(trimethylsilyl)acetamide (620 μL) was added at room temperature with stirring. The mixture was stirred at room temperature for 10 minutes and then cooled to about 0° C. To this mixture was added the above-mentioned carbonyl chloride (167 mg) and the mixture was stirred for 2 hours at 0° C. The reaction mixture was diluted with ethyl acetate (100 mL), and then washed with 0.2N hydrochloric acid (20 mL×1) and with water (20 mL×5). After drying over magnesium sulfate, the solvent was distilled off. The residue was dissolved in acetone (20 mL), and the solution was allowed to stand for 24 hours at room temperature. Acetone was distilled off. The residual solid was washed with ethyl ether and filtered off to yield the desired compound (229 mg).

Infrared absorption spectrum (cm$^{-1}$, nujol): 1770–1785, 1720, 1645, 1608

NMR spectrum (δ, DMSO-d$_6$):
1.41 (3H, s), 1.55 (3H, s), 2.33 (3H, s), 2.41 (3H, s), 4.19 (1H, s), 5.39 (1H, d, J=4.5 Hz), 5.44 (1H, d, J=8 Hz, 4.5 Hz), 5.77 (1H, d, J=7.5 Hz), 6.70 (2H, d, J=8.5 Hz), 7.23 (2H, d, J=8.5 Hz), 7.38 (1H, d, J=8.5 Hz), 7.95 (1H, d, J=8.5 Hz), 8.87 (1H, s)

EXAMPLE 23

7β-[D-2-(7,8-Diacetoxy-2-oxo-2H-1-benzopyran-3-carboxamide)-2-phenylacetamide]-3-acetoxymethyl-3-cephem-4-carboxylic acid.

Cephaloglycine (203 mg) was suspended in ethyl acetate (10 mL), to which N,O-bis(trimethylsilyl)acetamide (250 μL) was added at room temperature. After stirring for 10 minutes, the mixture was cooled to about 0° C. To this mixture was added 7,8-diacetoxy-2-oxo-2H-1-benzopyran-3-carbonyl chloride (167 mg), followed by stirring for 2 hours at 0° C. The reaction mixture was diluted with ethyl acetate (100 mL), and then washed with 0.2N hydrochloric acid (20 mL×1) and water (20 mL×5). After drying over magnesium sulfate, the solvent was distilled off. The residue was washed with ethyl ether and filtered off to yield the desired compound (313 mg).

Infrared absorption spectrum (cm$^{-1}$, nujol): 1770–1780, 1705–1720, 1655, 1605

NMR spectrum (δ, DMSO-d$_6$): 2.01 (3H, s), 2.35 (3H, s), 2.42 (3H, s), 3.37 (1H, d, J=18 Hz), 3.56 (1H, d, J=18 Hz), 4.65 (1H, d, J=13 Hz), 4.98 (1H, d, J=13 Hz), 5.02 (1H, d, J=5 Hz), 5.65–5.95 (1H, m), 7.2–7.6 (5H, m), 7.39 (1H, d, J=8.5 Hz), 7.95 (1H, d, J=8.5 Hz), 8.89 (1H, s)

EXAMPLE 24

7β-[D-2-(7,8-Diacetoxy-2-oxo-2H-benzopyran-3-carboxamide)-2-(4-hydroxyphenyl)acetamide]-3-(1-methyl-5-tetrazolyl)thiomethyl-3-cephem-4-carboxylic acid.

7β-[D-2-(Amino-2-(4-hydroxyphenyl)acetamide]-3-(1-methyl-5-tetrazolyl)thiomethyl-3-cephem-4-carboxylic acid trifluoroacetate (296 mg) was suspended in ethyl acetate (10 mL), to which N,O-bis(trimethylsilyl)acetamide (0.5 mL) was added at room temperature. After stirring for 10 minutes, the mixture was cooled to about 0° C. To this mixture was added 7,8-diacetoxy-2-oxo-2H-1-benzopyran-3-carbonyl chloride (167 mg) at 0° C. The mixture was stirred for 2 hours at 0° C. The reaction mixture was worked up described for Example 22 to yield the desired compound (380 mg).

Infrared absorption spectrum (cm$^{-1}$, nujol): 1770–1780, 1720, 1690, 1620, 1605

NMR spectrum (δ, DMSO-d$_6$): 2.35 (3H, s), 2.42 (3H, s), 3.62 (2H, br s), 3.92 (3H, s), 4.19 (1H, d, J=13 Hz), 5.01 (1H, d, J=5 Hz), 5.6–5.95 (2H, m), 6.71 (2H, d, J=8.5 Hz), 7.25 (2H, d, J=8.5 Hz), 7.39 (1H, d, J=8.5 Hz), 7.95 (1H, d, J=8.5 Hz), 8.89 (1H, s)

EXAMPLE 25

7β-[D-2-(7,8-Dihydroxy-2-oxo-2H-1-benzopyran-3-carboxamide)-2-(4-hydroxyphenyl)acetamide]-3-acetoxymethyl-3-cephem-4-carboxylic acid.

7,8-Dihydroxy-2-oxo-2H-1-benzopyran-3-carboxylic acid (50 mg) was heated under reflux for 5.5 hours in thionyl chloride (20 mL), and then thionyl chloride was distilled off. Benzene (10 mL) was added to the residues, and the benzene was distilled off, followed by vacuum drying, to yield 7,8-dihydroxy-2-oxo-2H-1-benzopyran-3-carbonyl chloride.

7β-[D-2-(Amino-2-(4-hydroxyphenyl)acetamide]-3-acetoxymethyl-3-cephem-4-carboxylic acid (200 mg) was suspended in ethyl acetate (40 mL). Trifluoroacetic acid (40 μL) and N,O-bis(trimethylsilyl)acetamide (0.4 mL) were added, followed by stirring for 10 minutes at room temperature and a further 20 minutes in an ice bath. This mixture was added to the ethyl acetate solution (10 mL) of the above-mentioned carbonyl chloride (whole amount), followed by stirring for 1 hour at room temperature. To the reaction mixture was added 1N hydrochloric acid (20 mL) and the mixture was extracted with ethyl acetate (100 mL). The organic layer was washed with water (50 mL×2) and with brine (50 mL×1). After drying over magnesium sulfate, the solvent was distilled off. The residue was dissolved in a small amount of acetone, and then solidified by adding ethyl ether and the precipitates were filtered off to yield the desired compound (110 mg).

Infrared absorption spectrum (cm$^{-1}$, nujol): 1760, 1710, 1660, 1610

NMR spectrum (δ, DMSO-d$_6$): 2.02 (3H, s), 4.65 (1H, d, J=14 Hz), 5.00 (1H, d, J=14 Hz), 5.03 (1H, d, J=5 Hz), 5.61–5.93 (2H, m), 6.75 (2H, d, J=8 Hz), 6.90 (1H, d, J=8 Hz), 7.26 (2H, d, J=8 Hz), 7.37 (1H, d, J=8 Hz), 8.77 (1H, s)

EXAMPLE 26

7β-[D-2-(7,8-Dihydroxy-2-oxo-2H-1-benzopyran-3-carboxamide)-2-(4-hydroxyphenyl)acetamide]-7α-methoxy-3-acetoxymethyl-3-cephem-4-carboxylic acid.

7β-[D-2-Amino-2-(4-hydroxyphenyl)acetamide]-7α-methoxy-3-acetoxymethyl-3-cephem-4-carboxylic acid trifluoroacetate (200 mg) was suspended in ethyl acetate (30 mL), to which N,O-bis(trimethylsilyl)acetamide (0.4 mL) was added. The mixture was stirred for 10 minutes at room temperature and for a further 10 minutes in an ice bath. This mixture was added to the ethyl acetate solution (10 mL) of 7,8-dihydroxy-2-oxo-2H-1-benzopyran-3-carbonyl chloride with ice cooling, followed by stirring for 1 hour at room temperature. The reaction mixture was worked up as described for Example 25 to yield the desired compound (86 mg).

Infrared absorption spectrum (cm$^{-1}$, nujol): 1760, 1700, 1600

NMR spectrum (δ, DMSO-d$_6$): 2.01 (3H, s), 3.42 (3H, s), 4.62 (1H, d, J=14 Hz), 4.91 (1H, d, J=14 Hz), 5.11 (1H, s), 5.67 (1H, d, J=8 Hz), 6.76 (2H, d, J=8 Hz), 6.90 (1H, d, J=8 Hz), 7.32 (2H, d, J=8 Hz), 7.37 (1H, d, J=8 Hz), 8.78 (1H, s), 9.38 (1H, d, J=8 Hz), 9.70 (1H, s)

EXAMPLE 27

7β-[D-(7,8-Dihydroxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid.

7β-[D-2-Amino-2-(4-hydroxyphenyl)acetamide]-3-(1-carboxymethyl-5-tetrazolyl)thiomethyl-3-cephem-4-carboxylic acid trifuloroacetate (300 mg) was suspended in ethyl acetate (40 mL), to which N,O-bis(trimethylsilyl)acetamide (0.5 mL) was added. The liquid was stirred for 10 minutes at room temperature and for a further 10 minutes in an ice bath. This mixture was added to ethyl acetate solution (10 mL) of 7,8-dihydroxy-2-oxo-2H-1-benzopyran-3-carbonyl chloride with ice cooling, followed by stirring for 1 hour at room temperature. The reaction mixture was worked up as described for Example 25 to yield the desired compound (107 mg).

Infrared absorption spectrum (cm$^{-1}$, nujol): 1760, 1710, 1610

NMR spectrum (δ, DMSO-d$_6$): 3.5 (1H, d, J=18 Hz), 3.7 (1H, d, J=18 Hz), 4.17 (1H, d, J=14 Hz), 4.45 (1H, d, J=14 Hz), 4.98 (1H, d, J=4.5 Hz), 5.26 (2H, s), 5.38–5.83 (2H, m), 6.71 (2H, d, J=8 Hz), 6.90 (1H, d, J=8 Hz), 7.24 (2H, d, J=8 Hz), 7.35 (2H, d, J=8 Hz), 8.75 (1H, s)

EXAMPLE 28

6β-[D-2-(6,7-Diacetoxy-2-oxo-2H-1-benzothiopyran-3-carboxamide)-2-phenylacetamide]penicillanic acid.

A mixture of 6,7-diacetoxy-2-oxo-2H-1-benzothiopyran-3-carboxylic acid (60 mg), thionyl chloride (40 μL), and dimethylformamide (one drop) was heated under reflux for 2 hours in benzene (15 mL), and then the solvent was distilled off. Benzene (15 mL) was added to the residue, and the benzene was distilled off again, followed by vacuum drying to yield 6,7-diacetoxy-2-oxo-2H-1-benzothiopyran-3-carbonyl chloride.

Amcipillin trihydrate (72 mg) was suspended in tetrahydrofuran (15 mL) to which N,O-bis(trimethylsilyl)acetamide (230 μL) was added. After stirring for 3.5 hours at room temperature, the mixture was cooled with ice. To this mixture was added tetrahydrofuran solution (10 mL) of the above-mentioned carbonyl chloride. The mixture was stirred for 1 hour with ice cooling and for a further 1 hour at room temperature. The reaction mixture was concentrated to about 5 mL and the concentrated mixture was added into 0.2N hydrochloric acid (40 mL) with stirring and ice cooling. The separated solid was filtered off and washed with water and dried to yield the desired compound (71 mg).

Infrared absorption spectrum (cm$^{-1}$, nujol): 1770, 1650

NMR spectrum (δ, DMSO-d$_6$): 1.42 (3H, s), 1.56 (3H, s), 2.35 (6H, s), 4.20 (1H, s), 5.38 (1H, d, J=5 Hz), 7.19–7.50 (5H, m), 7.82 (1H, s), 8.16 (1H, s), 8.84 (1H, s)

EXAMPLE 29

7β-[D-2-(6,7-Diacetoxy-2-oxo-2H-1-benzothiopyran-3-carboxamide)-2-(4-hydroxyphenyl)acetamide]-3-(1-carboxymethyl)-5-tetrazolyl)thiomethyl-3-cephem-4-carboxylic acid.

7β-[D-2-Amino-2-(4-hydroxyphenyl)acetamide]-3-(1-carboxymethyl)-5-tetrazolyl)thiomethyl-3-cephem-4-carboxylic acid (162 mg) was suspended in tetrahydrofuran (30 mL), to which N,O-bis(trimethylsilyl)acetamide (310 μL) was added. The liquid was stirred for 4 hours at room temperature and then cooled with ice. The mixture was treated with 6,7-diacetoxy-2-oxo-2H-1-benzothiopyran-3-carbonylchloride as in Example 28 to yield the desired compound (87 mg).

Infrared absorption spectrum (cm$^{-1}$, nujol): 1760, 1650

NMR spectrum (δ, DMSO-d$_6$): 2.30 (3H, s), 2.35 (3H, s), 4.16 (1H, d, J=14 Hz), 4.45 (1H, d, J=14 Hz), 4.97 (1H, d, J=7 Hz), 5.26 (2H, s), 5.60–5.76 (2H, m), 6.70 (2H, d, J=9 Hz), 7.83 (1H, s), 8.15 (1H, s), 8.85 (1H, s)

EXAMPLE 30

7β-[D-2-(6,7-Dihydroxy-2-oxo-2H-1-benzothiopyran-3-carboxamide)-2-(4-hydroxyphenyl)acetamide]-3-(1-carboxymethyl)-5-tetrazolyl)thiomethyl-3-cephem-4-carboxylic acid.

7β-[D-2-(6,7-Diacetoxy-2-oxo-2H-1-benzothiopyran-3-carboxamide)-2-(4-hydroxyphenyl)acetamide]-3-(1-carboxymethyl)-5-tetrazolyl)thiomethyl-3-cephem-4-carboxylic acid (60 mg) which was obtained in Example 29 was suspended in methylene chloride (10 mL). Dihydropyran (190 mg) and p-toluenesulfonic acid (3 mg) were added, followed by stirring for 3.5 hours at room temperature. Then, the solvent was removed by distillation. To the residue were added ethanol-water (1:1, 9 mL) and sodium hydrogen carbonate (30 mg). After stirring for 2 hours at 50° C., the reaction mixture was concentrated to about 5 mL and 0.25N hydrochloric acid (20 mL) was added with ice cooling. The separated solids were filtered off and dissolved in methanol (5 mL). A catalytic amount of p-toluenesulfonic acid was added and the solution was stirred overnight. Most of methanol was distilled off, and then ethyl ether was added. The separated solids were filtered off to yield the desired compound (38 mg).

Infrared absorption spectrum (cm$^{-1}$, nujol): 1760, 1640

NMR spectrum (δ, DMSO-d$_6$): 4.96 (1H, d, J=5 Hz), 5.27 (2H, s), 5.60–5.75 (2H, m), 6.70 (2H, d, J=9 Hz), 7.02 (1H, s), 7.23 (2H, d, J=9 Hz), 7.40 (1H, s), 8.70 (1H, s)

EXAMPLE 31

7β-[D-2-(6,7-Diacetoxy-2-oxo-2H-1-benzothiopyran-3-carboxamide)-2-(4-hydroxyphenyl)acetamide]-3-(1-methyl-5-tetrazolyl)thiomethyl-3-cephem-4-carboxylic acid.

7β-[D-2-Amino-2-(4-hydroxyphenyl)acetamide]-3-(1-methyl-5-tetrazolyl)thiomethyl-3-cephem-4-carboxylic acid (128 mg) was reacted with 6,7-diacetoxy-2-oxo-2H-1-benzothiopyran-3-carbonyl chloride as in Example 28 to yield the desired compound (44 mg).

Infrared absorption spectrum (cm$^{-1}$, nujol): 1760, 1720, 1710, 1650

NMR spectrum (δ, DMSO-d$_6$): 2.35 (6H, s), 3.50 (1H, d, J=18 Hz), 3.72 (1H, d, J=18 Hz), 3.92 (3H, s), 4.20 (1H, d, J=14 Hz), 4.36 (1H, d, J=14 Hz), 5.01 (1H, d, J=5 Hz), 5.61–5.81 (2H, m), 6.71 (2H, d, J=9 Hz), 7.25 (2H, d, J=9 Hz), 7.82 (1H, s), 8.16 (1H, s), 8.85 (1H, s)

EXAMPLE 32

7β-[D-2-(6,7-Diacetoxy-1,2-dihydro-2-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

A mixture of 6,7-diacetoxy-1,2-dihydro-2-oxoquinoline-3-carboxylic acid (100 mg), thionyl chloride (70 μL), and dimethylformamide (one drop) was heated under reflux for 4.5 hours in 50 mL of benzene, and the solvent was distilled off. Benzene (30 mL) was added to the residue and the benzene was distilled off again, followed by vacuum drying, to yield 6,7-diacetoxy-1,2-dihydro-2-oxoquinoline-3-carbonyl chloride.

7β-[D-2-Amino-2-(4-hydroxyphenyl)acetamide]-3-[5-methyl-2-(1,3,4-thiadiazolyl)]thiomethyl-3-cephem-4-carboxylic acid (162 mg) was suspended in tetrahydrofuran (30 mL), to which N,O-bis(trimethylsilyl)acetamide (330 μL) was added. After stirring for 6 hours at room temperature, the mixture was cooled with ice. To this mixture was added the tetrahydrofuran solution (20 mL) of the above-mentioned carbonyl chloride (whole amount). The reactants were stirred for 2 hours with ice cooling and for a further 1 hour at room temperature. The reaction mixture was concentrated to about 5 mL, and the concentrated solution was added dropwise to 0.2N hydrochloric acid (40 mL) with stirring and ice cooling. The separated solids were filtered off, followed by washing and drying, to yield the desired compound (210 mg).

Infrared absorption spectrum (cm$^{-1}$, nujol): 1780, 1760, 1680

NMR spectrum (δ, DMSO-d$_6$): 2.37 (6H, s), 2.70 (3H, s), 4.17 (1H, d, J=14 Hz), 4.52 (1H, d, J=14 Hz), 5.04 (1H, d, J=5 Hz), 5.65–5.83 (2H, m), 6.72 (2H, d, J=9 Hz), 7.32 (2H, d, J=9 Hz), 7.90 (1H, s), 8.02 (1H, s), 8.52 (1H, s)

EXAMPLE 33

7β-[D-2-(6,7-Diacetoxy-1,2-dihydro-2-oxoquinoline-3-carboxamide)-2-(4-hydroxyphenyl)acetamide]-3-(1-carboxymethyl-5-tetrazolyl)thiomethyl-3-cephem-4-carboxylic acid.

7β-[D-2-Amino-2-(4-hydroxyphenyl)acetamide]-3-(1-carboxymethyl-5-tetrazolyl)thiomethyl-3-cephem-4-carboxylic acid (170 mg) was reacted with 6,7-diacetoxy-1,2-dihydro-2-oxoquinoline-3-carbonyl chloride as in Example 32 to yield the desired compound (61 mg).

Infrared absorption spectrum (cm$^{-1}$, nujol): 1760, 1720, 1700, 1620

NMR spectrum (δ, DMSO-d$_6$): 2.36 (6H, s), 3.52–3.68 (2H, m), 4.18 (1H, d, J=14 Hz), 4.45 (1H, d, J=14 Hz), 5.00 (1H, d, J=5 Hz), 5.60–5.85 (2H, m), 6.72 (2H, d, J=9 Hz), 7.30 (2H, d, J=9 Hz), 7.95 (1H, s), 8.11 (1H, s), 8.99 (1H, s)

EXAMPLE 34

7β-[D-2-(6,7-Dihydroxy-1,2-dihydro-2-oxoquinoline-3-carboxamide)-2-(4-hydroxyphenyl)acetamide]-3-[5-methyl-2-(1,3,4-thiadiazolyl)]thiomethyl-3-cephem-4-carboxylic acid.

7β-[D-2-(6,7-Diacetoxy-1,2-dihydro-2-oxoquinoline-3-carboxamide)-2-(4-hydroxyphenyl)acetamide]-3-[5-methyl-2-(1,3,4-thiadiazolyl)]thiomethyl-3-cephem-4-carboxylic acid (78 mg) was treated as in Example 30 to yield the desired compound (37 mg).

Infrared absorption spectrum (cm$^{-1}$, nujol): 1760, 1620

NMR spectrum (δ, DMSO-d$_6$): 2.70 (3H, s), 4.18 (1H, d, J=14 Hz), 4.52 (1H, d, J=14 Hz), 5.03 (1H, d, J=5 Hz), 5.65–5.78 (2H, m), 6.72 (2H, d, J=9 Hz), 7.31 (2H, d, J=9 Hz), 7.16 (1H, s), 7.21 (1H, s), 8.15 (1H, s)

EXAMPLE 35

7β-[D-2-(6,7-Diacetoxy-1-methyl-1,2-dihydro-2-oxoquinoline-3-carboxamide)-2-(4-hydroxyphenyl)acetamide]-3-acetoxymethyl-3-cephem-4-carboxylic acid.

A mixture of 6,7-diacetoxy-1-methyl-1,2-dihydro-2-oxoquinoline-3-carboxylic acid (60 mg), thionyl chloride (40 μL), and dimethylformamide (one drop) was heated under reflux for 2 hours in 40 mL of benzene, and the solvent was distilled off. Benzene (30 mL) was added to the residue and the benzene was distilled off again, followed by vacuum drying, to yield 6,7-diacetoxy-1-methyl-1,2-dihydro-2-oxoquinoline-3-carbonyl chloride.

7β-[D-2-Amino-2-(4-hydroxyphenyl)acetamide]-3-acetoxymethyl-3-cephem-4-carboxylic acid (80 mg) was suspended in tetrahydrofuran (20 mL), and N,O-bis(trimethylsilyl)acetamide (190 μL) was added. After stirring for 20 minutes at room temperature, the liquid was cooled with ice. To this liquid was added the tetrahydrofuran solution (10 mL) of the above-mentioned carbonyl chloride (whole amount). The reaction mixture was stirred for 2 hours with ice cooling. The reaction mixture was concentrated to about 5 mL, and the concenetrated solution was added dropwise to 0.2N hydrochloric acid (30 mL) with stirring and ice cooling. The separated solids were filtered off, followed by washing with water and drying, to yield the desired compound (100 mg).

Infrared absorption spectrum (cm$^{-1}$, nujol): 1760, 1640, 1620

NMR spectrum (δ, DMSO-d$_6$): 2.01 (3H, s), 2.28 (3H, s), 2.32 (3H, s), 3.70 (3H, s), 4.62 (1H, d, J=14 Hz), 4.95 (1H, d, J=14 Hz), 5.00 (1H, d, J=5 Hz), 5.57–5.80 (2H, m), 6.69 (2H, d, J=9 Hz), 7.23 (2H, d, J=9 Hz), 7.60 (1H, s), 7.92 (1H, s), 8.78 (1H, s)

EXAMPLE 36

6β-[D-2-(6,7-Dihydroxy-2-oxo-2H-1-benzopyran-3-carboxamide)-2-(4-hydroxyphenyl)acetamide]penicillanic acid pivaloyloxymethyl ester.

6β-[D-2-(6,7-Dihydroxy-2-oxo-2H-1-benzopyran-3-carboxamide)-2-(4-hydroxyphenyl)acetamide]pencillanic acid (40 mg) obtained in Example 18 was dissolved in dimethylformamide (0.2 mL). Sodium hydrogen carbonate (7.1 mg), chloromethyl pivalate (30 μL), and sodium iodide (2 mg) were added. The mixture was stirred for 2 days at room temperature. The reaction mixture was diluted with ethyl acetate (80 mL), and washed with water (20 mL×1), with 2% aq. solution of sodium acetate (20 mL ×2), with 0.5N hydrochloric acid once, and with water (20 mL ×3). After drying over magnesium sulfate, the ethyl acetate was distilled off. The residue was solidified with ether to yield the desired compound (10 mg).

Infrared absorption spectrum (cm$^{-1}$, nujol): 1760, 1730, 1680, 1615

NMR spectrum (δ, DMSO-d$_6$): 1.14 (9H, s), 1.37 (3H, s), 1.55 (3H, s), 4.39 (1H, s), 5.44 (1H, d, J=4 Hz), 5.5–6.0 (4H, m), 6.72 (2H, d, J=8 Hz), 6.83 (1H, s), 7.22 (2H, d, J=8 Hz), 7.28 (1H, s), 8.84 (1H, s)

Tables 1 and 2 show the antibacterial activity (MIC, μg/mL) of the compounds of this invention. In these tables, the compounds of this invention are represented by the Example Nos. The control compound in Table 1 is D(−)-α-(4-hydroxy-1,5-naphthyridine-3-carboxamide)benzylpenicillin which has the highest antibacterial activity against Pseud. aeruginosa according to the above-mentioned known literature and is being developed as an antibacterial medicine, and the control compound in Table 2 is D(−)-α-(coumarin-3-carboxamide)benzylpenicillin which is considered to be highest in antibacterial activity against Kleb. pneumoniae and Pseud. aeruginosa according to the above-mentioned known literature.

As shown in Table 1, the antibacterial activity of the compound of this invention is about 15 to 260 times higher for Kleb. pneumoniae and about 4 to 8 times higher for Pseud. aeruginosa as compared with the control compound.

As shown in Table 2, the antibacterial activity of the compound of this invention is about 15 to 1,000 times higher for Kleb. pneumoniae and about 4 to 15 times hihger for Pseud. aeruginosa as compared with the control compound.

TABLE 1

| | Test bacteria MIC (μg/mL) | | | |
|---|---|---|---|---|
| | Kleb. pneumoniae EK-6 | Pseud. aerugi-nosa EP-067 | Pseud. aerugi-nosa EP-069 | Pseud. aerugi-nosa EP-071 |
| Compounds tested | | | | |
| Example 2 | 0.2 | 1.56 | 3.13 | 0.1 |
| Example 5 | 0.024 | 3.13 | 3.13 | 0.2 |
| Example 6 | 0.05 | 3.13 | 3.13 | 0.2 |
| Example 10 | ≦0.012 | 3.13 | 3.13 | 0.2 |
| Example 11 | 0.024 | 3.13 | 3.13 | 0.2 |
| Example 12 | 0.024 | 3.13 | 3.13 | 0.2 |
| Control compound | | | | |
| D(−)-α-(4-hydroxy-1,5-naphthyridine-3-carboxamide)benzyl-penicillin | 3.13 | 12.5 | 12.5 | 0.8 |

TABLE 1-continued

| | Test bacteria MIC (μg/mL) | | | |
|---|---|---|---|---|
| | Kleb. pneumoniae EK-6 | Pseud. aerugi-nosa EP-067 | Pseud. aerugi-nosa EP-069 | Pseud. aerugi-nosa EP-071 |

TABLE 2

| | Test bacteria MIC (μg/mL) | | | |
|---|---|---|---|---|
| | Kleb. pneumoniae EK-6 | Pseud. aerugi-nosa EP-067 | Pseud. aerugi-nosa EP-069 | Pseud. aerugi-nosa EP-071 |
| Compounds tested | | | | |
| Example 14 | 0.2 | 1.56 | 1.56 | 0.2 |
| Example 20 | 0.2 | 0.8 | 0.8 | 0.2 |
| Example 25 | 0.1 | 0.8 | 1.56 | 0.1 |
| Example 27 | ≦0.012 | 1.56 | 1.56 | 0.1 |
| Example 28 | 0.1 | 1.56 | 3.13 | 0.1 |
| Example 34 | 0.4 | 3.13 | 3.13 | 0.4 |
| Example 35 | 0.8 | 3.13 | 1.56 | 0.2 |
| Control compound | | | | |
| D(−)-α-(coumarin-3-carbienamido)-benzylpenicillin | 12.5 | 12.5 | 12.5 | 1.56 |

What is claimed is:

1. A compound represented by the formula:

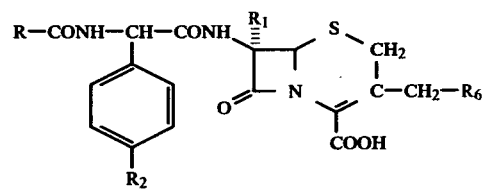

wherein R$_1$ is hydrogen or methoxy; R$_2$ is hydrogen or hydroxy; R is

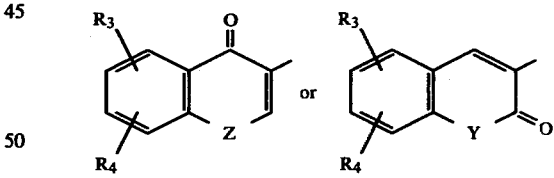

wherein R$_3$ and R$_4$ are hydroxy or acyloxy, Y is oxygen, sulfur or =N-R$_5$ wherein R$_5$ is hydrogen or lower alkyl, and Z is =N-R$_5$ wherein R$_5$ has the same meanings as defined above; and R$_6$ is acyloxy or substituted or unsubstituted nitrogen-containing heterocyclicthio, a pharmaceutically acceptable salt thereof, or a carboxylic ester thereof.

2. A compound according to claim 1, wherein R$_6$ is selected from the group consisting of pyrrolyl, pyridyl and N-oxide thereof, imidazolyl, pyrazolyl, pyrimidinyl, pyridazinyl, 1H-1,2,4-triazolyl, 4H-1,2,4-triazolyl, 1H-1,2,3-triazolyl, 2H-1,2,3-triazolyl, 1H-tetrazolyl, 2H-tetrazolyl, thiazolyl, 1,2,3-thiazolyl, 1,2,4-thiazolyl, 1,3,4-thiadiazolyl, oxazolyl, 1,3,4-oxadiazolyl, 1,2,5-oxadiazolyl, morpholino, benzothiazolyl, and benzoxazolyl, which groups may be unsubstituted or substituted by a member selected from the group consisting of methyl, ethyl, propyl, isopropyl, amino, dimethylaminoethyl, dimethylaminomethyl, diethylaminoethyl, carboxymethyl, carboxyethyl, sulfomethyl and sulfoethy.

3. A compound according to claim 1 wherein both $R_3$ and $R_4$ are hydroxy.

4. A compound according to claim 3, wherein said compound is 7β-[D-2-(6,7-dihydroxy-1-ethyl-1,4-dihydro-4-oxoquinoline-3-carboxamide)-2-(4-hydroxyphenyl)acetamide]-3-[5-methyl-2-(1,3,4-thiadiazolyl)]-thiomethyl-3-cephem-4-carboxylic acid or pharmaceutically acceptable salt thereof.

5. A compound according to claim 3, wherein said compound is 7β-[D-2-(6,7-dihydroxy-4-oxo-4H-1-benzothiopyran-3-carboxamide)-2-(4-hydroxyphenyl)acetamide]-3-(1-methyl-5-tetrazolyl)thiomethyl-3-cephem-4-carboxylic acid or pharmaceutically acceptable salt thereof.

6. A compound according to claim 3, wherein said compound is 7β-[D-2-(6,7-dihydroxy-4-oxo-4H-1-benzothiopyran-3-carboxamide)-2-(4-hydroxyphenyl)acetamide]-3-(1-carboxymethyl-5-tetrazolyl)thiomethyl-3-cephem-4-carboxylic acid or pharmaceutically acceptable thereof.

7. A compound according to claim 3, wherein said compound is 7β-[D-2-(6,7-dihydroxy-2-oxo-2H-1-benzopyran-3-carboxamide)-2-(4-hydroxyphenyl)acetamide]-3-(1-carboxymethyl-5-tetrazolyl)thiomethyl-3-cephem-4-carboxylic acid or pharmaceutically acceptable salt thereof.

8. A compound according to claim 1, wherein said compound is 7β-[D-2-(7,8-dihydroxy-2-oxo-2H-1-benzopyran 3-carboxamide)-2-(4-hydroxyphenyl)acetamide]-3-acetoxymethyl-3-cephem-4-carboxylic acid or pharmaceutically acceptable salt thereof.

9. A compound according to claim 3, wherein said compound is 7β-[D-2-(7,8-dihydroxy-2-oxo-2H-1-benzopyran-3-carboxamide)-2-(4-hydroxyphenyl)acetamide]-7α-methoxy-3-acetoxymethyl-3-cephem-4-carboylic acid or pharmaceutically acceptable salt thereof.

10. A compound according to claim 3, wherein said compound is 7β-[D-(7,8-dihydroxy-2-oxo-2H-1-benzyopyran-3-carboxamide)-2-(4-hydroxyphenyl)acetamide]-3-(1-carboxymethyl-5-tetrazolyl)thiomethyl-3-cephem-4-carboxylic acid or pharmaceutically acceptable salt thereof.

11. A compound according to claim 3, wherein said compound is 7β-[D-2-(6,7-dihydroxy-2-oxo-2H-1-benzothiopyran-3-carboxamide)-2-(4-hydroxyphenyl)acetamide]-3-(1-carboxymethyl)-5-tetrazolyl)thiomethyl-3-cephem-4-carboxylic acid or pharmaceutically acceptable salt thereof.

12. A compound according to claim 3, wherein said compound is 7β-[D-2-(6,7-dihydroxy-1,2-dihydro-2-oxoquinoline-3-carboxamide)-2-(4-hydroxyphenyl)acetamide]-3-[5-methyl-2-(1,3,4-thiadiazolyl)]thiomethyl-3-cephem-4-carboxylic acid or pharmaceutically acceptable salt thereof.

13. An antibacterial composition which comprises an antibacterially effective amount of a compound or pharmaceutically acceptable salt or ester thereof as defined in claim 1 and a pharmaceutically acceptable carrier therefor.

14. A process for preparing a compound represented by the formula:

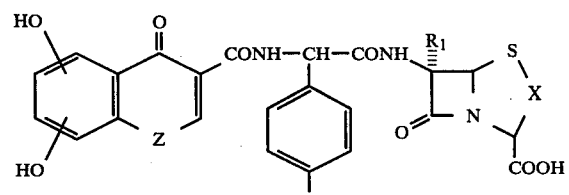

or

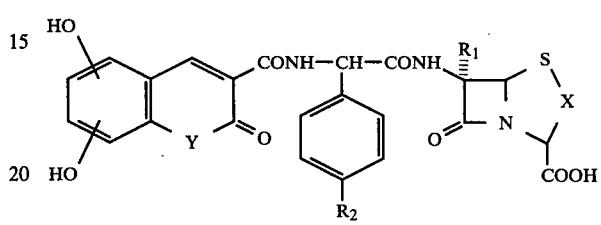

wherein $R_1$ is hydrogen or methyl; $R_2$ is hydrogen or hydroxy; and Y is oxygen, sulfur or >N-$R_5$ wherein $R_5$ is hydrogen or lower alkyl, and Z is sulfur or >N-$R_5$ wherein $R_5$ has the same meanings as defined above; and X is

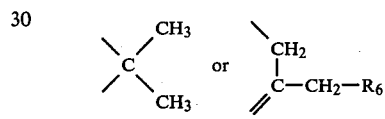

wherein $R_6$ is acyloxy or nitrogen-containing hetrocyclicthio which may have substituent(s), a pharmaceutically acceptable salt thereof, or a carboxylic ester thereof, which comprises hydrolyzing a compound represented by the formula:

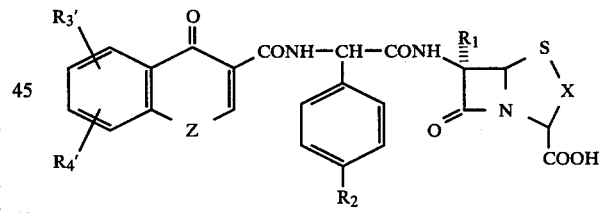

or

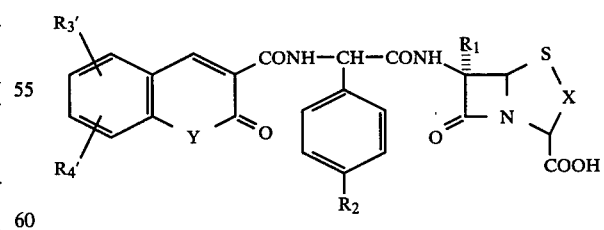

wherein $R_1$, $R_2$, X, Y and Z have the same meanings as defined above, $R_3'$ and $R_4'$ are acyloxy, in the presence of a base, and if desired, followed by salt formation or esterification.

* * * * *